United States Patent
Eschenhagen

(10) Patent No.: US 7,618,452 B2
(45) Date of Patent: Nov. 17, 2009

(54) ARTIFICIALLY PRODUCED, THREE-DIMENSIONAL MUSCLE TISSUE

(75) Inventor: Thomas Eschenhagen, Erlangen (DE)

(73) Assignee: Medigene AG, Martinsried (DE)

( * ) Notice: Subject to any disclaimer, the term of this patent is extended or adjusted under 35 U.S.C. 154(b) by 1037 days.

(21) Appl. No.: 10/182,131

(22) PCT Filed: Jan. 26, 2001

(86) PCT No.: PCT/EP01/00856

§ 371 (c)(1), (2), (4) Date: Oct. 3, 2002

(87) PCT Pub. No.: WO01/55297

PCT Pub. Date: Aug. 2, 2001

(65) Prior Publication Data

US 2003/0091979 A1 May 15, 2003

(30) Foreign Application Priority Data

Jan. 27, 2000 (DE) .................................. 100 03 521

(51) Int. Cl.
*A61F 2/08* (2006.01)
(52) U.S. Cl. .................. 623/14.13; 623/11.11; 435/325; 435/395; 424/93.1; 424/93.7
(58) Field of Classification Search .............. 435/366, 435/395, 325; 424/93.7
See application file for complete search history.

(56) References Cited

U.S. PATENT DOCUMENTS

| | | |
|---|---|---|
| 3,540,985 A | 11/1970 | Gross |
| 3,902,972 A | 9/1975 | Beckford |
| 3,985,608 A | 10/1976 | Saxholm |

(Continued)

FOREIGN PATENT DOCUMENTS

DE 19500498 A1 7/1996

(Continued)

OTHER PUBLICATIONS

Powell et al, "Tissue-Engineered Human Bioartificial Muscles Expressing a Foreign Recombinant Protein for Gene Therapy" Human Gene Therapy, Mar. 1999, vol. 10, pp. 565-577.*

(Continued)

*Primary Examiner*—Allison M Ford
(74) *Attorney, Agent, or Firm*—Clark & Elbing LLP

(57) ABSTRACT

The invention relates to a device for producing a three-dimensional circular muscle body from a carrier substance and from cell cultures incorporated therein comprising a cell culture dish (1) and at least one element (2) placed inside said cell culture dish (1). The invention also relates to a multi-well plate constructed of a number of devices, which are arranged side by side and/or one behind the other, for producing a three-dimensional circular muscle body. The invention additionally relates to a solution for cultivating mammal cardiomyocytes, to a method for cultivating a cell culture, to a device for measuring isometric force parameters of cell cultures, and to a method for following, in a measurable manner, contractions of a cell tissue incorporated in a carrier substance. Finally, the invention relates to an artificially produced three-dimensional muscle tissue, in particular, a heart muscle tissue.

15 Claims, 7 Drawing Sheets

U.S. PATENT DOCUMENTS

| | | | |
|---|---|---|---|
| 4,140,582 A | | 2/1979 | Saxholm |
| 4,975,377 A | | 12/1990 | Key |
| 5,153,136 A | | 10/1992 | Vanderburgh |
| 5,605,836 A | | 2/1997 | Chen et al. |
| 6,034,053 A | * | 3/2000 | Uckun et al. ............ 514/2 |
| 6,866,842 B1 | * | 3/2005 | Chancellor et al. ........ 424/93.1 |

FOREIGN PATENT DOCUMENTS

| | | | |
|---|---|---|---|
| DE | 19843234 A1 | | 3/2000 |
| DE | 19903506 A1 | | 8/2000 |
| EP | 0218065 A2 | | 4/1987 |
| EP | 0751215 A2 | | 1/1997 |
| JP | 02 154679 | | 6/1990 |
| JP | 06 032345 | | 2/1994 |
| WO | WO 98/54301 | * | 12/1998 |

OTHER PUBLICATIONS

Zimmerman et al, "Three-Dimensional Engineered Heart Tissue from Neonatal Rat Cardiac Myocytes" Biotechnology Bioengineering, Apr. 2000, vol. 68, pp. 106-114.*

International Preliminary Examination Report for PCT/EP01/00856 dated Apr. 26, 2002.

German Official Action dated Dec. 29, 2000.

* cited by examiner

ARTIFICIALLY PRODUCED, THREE-DIMENSIONAL MUSCLE TISSUE

The present invention relates to a device for producing a three-dimensional matrix or muscle body, to a multiwell plate for producing a plurality of three-dimensional matrix or muscle bodies, to a solution for cultivating mammalian cardiomyocytes, to a method for cultivating a cell culture, to a device for measuring isometric force parameters, to a method for the measurable following of contractions and to an artificially produced three-dimensional muscle tissue.

Cardiac insufficiency is, with an estimated prevalence of 1.5 to 2% of the population, one of the principal causes of morbidity and mortality in the western world. Cardiac insufficiency is always either the consequence of a primary increase in the stress on the heart or the consequence of destruction or damage to myocardial cells (cardiomyocytes), which, while the body's requirement for the overall contractile performance of the heart remains the same, leads secondarily to an increased stress on the remaining, undamaged myocardial cells.

This has two considerable consequences. On the one hand, the increased stress leads to a growth in size, i.e. to a hypertrophy, of the remaining, undamaged myocardial cells. On the other hand, there is a large number of quantitative changes in gene expression, i.e. a disease-specific phenotype of the remaining, undamaged myocardial cells. These specific changes in gene expression and their consequences for the function of the myocardial cells are known only in small part. The only clear point in this connection to date is that each individual cell (and not just the whole organ the heart) of a failing heart differs from those of a healthy heart.

Therapeutic efforts to date for the treatment of cardiac insufficiency aim essentially at relieving the hemodynamic load on the diseased heart and pharmacologically suppressing the mechanisms which have been recognized as causing the changes in gene expression and the hypertrophy (activation of neurohumoral systems such as sympathetic nervous system, renin-angiotensin-aldosterone system, endothelin, growth factors, inflammatory mediators). It is in fact possible in this way to delay the natural progress of the disorder. It must be taken into account in this connection that the activation of the aforementioned processes on the one hand certainly represent sensible adaptations with which a diseased heart responds to the increased stress. On the other hand, however, it is the same mechanisms which eventually contribute to an increased destruction of myocardial cells and thus initiate a vicious circle which explains the poor prognosis of patients with cardiac insufficiency.

Novel therapeutic approaches to the treatment of cardiac insufficiency therefore aim at identifying specific targets in the heart which lead exclusively or predominantly to a diminished function of the heart or to an increased rate of destruction of myocardial cells, and distinguishing these processes from processes which rather represent sensible adaptations of the diseased heart. For this purpose, various pharmaceutical companies have in the past employed systematic gene screening methods to look for differences in the gene expression of failing and healthy human hearts (subtractive methods). With the introduction of DNA chip technology there will be, in conjunction with the human genome project, a rapid increase in the near future in the number of new genes of unknown function and pathophysiological significance.

There is thus a great need for methods which permit rapid and efficient target validation. This means that the wish is to obtain relatively quickly information about the functional significance of quantitative changes in gene expression of unknown genes or genes about which little is known in myocardial cells and, proceeding beyond this, test the effect of substances which display an effect on the products of these genes.

The German patent DD 299 439 A5 describes a method for investigating medical pharmaceutical products on assemblages of cells, which are cultivated in vitro, from mammals, specifically the mouse, in which the effect of these products on pulsating, differentiated myocardial cells is investigated by observation. A cell line of such pluripotent, embryonic stem cells which is able to differentiate into spontaneously pulsating myocardial cells is used for this purpose. Embryoid bodies are cultivated in a suitable manner from the embryonic stem cells and can then be exposed to the active substance to be investigated, making in vivo investigations no longer necessary. The procedure described in DD 299 439 A5 does not, however, permit a statement to be made about the effect of the investigated active substances on the force of contraction of the myocardial cells. Merely the change in the pulse rate is investigated using a stopclock.

The German published specification DE 195 00 498 A1 describes for the first time how muscle tissue cells can be cultivated in such a way that measurements of the isometric force parameters and the influencing thereof are possible thereon. For this purpose, the aforementioned published specification shows matrix or muscle bodies which have two plate-shaped holding parts which are arranged in parallel and can be suspended in a clamping and measuring device, a matrix which is clamped between them and is composed of solidified collagen gel, and muscle tissue which is embedded therein and is produced by cultivation, the matrix being connected to the holding parts. The two plate-shaped holding parts consist of nonporous material and are either solid or hollow. To make it possible to suspend the holdings in a clamping and measuring device, tubular elements are formed thereon. In order to produce a connection with high tensile strength between the matrix and the holding parts, the surfaces of the holding parts are provided with self-hooking parts. In addition, spacers are provided between the holding parts, and these keep the distance between the holding parts constant during production of the matrix body and can be removed for measurement of isometric force parameters of the cell tissue. DE 195 00 498 A1 also discloses a method for cultivating cardiomyocytes in collagen gel, in particular for the measurable following of the contraction of myocardial tissue, and a device for producing a matrix body composed of collagen gel and incorporated cell cultures.

It became possible for the first time with the devices and methods described in DE 195 00 498 A1 to reconstruct chick myocardial cells in vitro to give an artificial three-dimensional myocardial tissue (so-called engineered heart tissue, "EHT"). This provided a three-dimensional, highly crosslinked, electrically connected structure which thus came close to the physiological conditions in vivo. Before this, myocardial cells were cultivated in a single layer in plastic dishes (so-called two-dimensional culture).

It was additionally possible with the devices and methods disclosed in DE 195 00 498 A1 to suppress overgrowth of the cardiomyocytes by fibroblasts in the presence of serum and growth factors. This allows substantially physiological growth and differentiation conditions without the need to employ cytostatics. In standard two-dimensional culture there is normally extensive overgrowth of the myocardial cells, which are unable to divide, by actively dividing fibroblasts, smooth muscle cells and endothelial cells. In conventional two-dimensional cultures, this is normally suppressed by removing serum and adding cytostatics.

It was also possible with the device disclosed in DE 195 00 498 A1 to measure force, frequency, contraction kinetics and diastolic tension in myocardial cells reliably and reproducibly under isometric conditions. This permitted a considerably more differentiated and valid assessment of the function of myocardial cells than would have been possible with neonatal or freshly isolated adult cardiomyocytes. For example, in a two-dimensional culture of neonatal myocardial cells it is possible to measure the frequency to only a very limited extent and the force not at all. With adult, freshly isolated myocardial cells it is possible to measure in a period of up to 6, maximally 24, hours relatively reliably the extent of the shortening as a parameter of the isotonic force. Since, however, myocardial cells are normally integrated in tissue, the contraction is never isotonic but usually predominantly isometric with a small isotonic component. Thus, compared with intact preparations and isolated cells, the advantage with the three-dimensional cell assemblages is that the situation is stable for days to weeks, which is particularly important for genetic manipulations.

Moreover the apparatuses and methods described in DE 195 00 498 A1, unlike intact preparations, allow good microscopic accessibility in situ and after histological staining.

Finally, it was also possible to show that the EHT disclosed in the cited German published specification displays excellent gene transfer efficiency with adenoviruses (100% of the living cells).

Despite the advantages and advances described above compared with a two-dimensional culture, the three-dimensional cell assemblages disclosed in DE 195 00 498 A1 still display a number of disadvantages. Thus, it has been possible to date to produce three-dimensional artificial heart tissues only from chick myocardial cells and not from mammalian myocardial cells. In addition, the production of EHT using the device described in DE 195 00 498 A1 is relatively laborious because it is necessary first to assemble tubes with a metal bracket and then fasten the tubes with a hook and loop tape and align them in wells in a cell culture dish, and it is then necessary to pipette a collagen/cell mixture into the wells. The devices must be discarded after being used a maximum of five times. Since the individual components of the devices disclosed in DE 195 00 498 A1 are fabricated manually, they are subject to a certain variability having an influence on the measured result. The junction between hook and loop tape and cardiac tissue moreover does not correspond to physiological conditions. Finally, the apparatus disclosed in the aforementioned German published specification is relatively complicated to manipulate and the design is such that a size below a certain minimum is not possible.

The object on which the present invention is based is thus to provide devices and methods which do not have the disadvantages described above. The intention of the present invention is, in particular, to create a device which can be assembled easily, can be manipulated easily, is miniaturizable, is subject to minimal design variations, can potentially be reused indefinitely and comes as close as possible to physiological conditions for producing three-dimensional cell tissues. It is further intended according to the invention to indicate conditions under which mammalian myocardial cells can be cultured as three-dimensional cell culture tissues. Finally, it is also intended to describe devices and methods allowing measurement under isometric conditions of force parameters of muscle tissues in cell cultures.

It has now been found, surprisingly, that muscle cells which are cultivated under suitable conditions in a cell culture dish with at least one element arranged in the cell culture dish form a three-dimensional muscle cell tissue around this element. This muscle cell tissue is so stable that, if required, it can be taken out manually and subjected to physiological, pharmacological and/or biotechnological experiments or even be transplanted.

The device of the invention for producing a three-dimensional, circular muscle body from a support substance and cell cultures incorporated therein has a cell culture dish and at least one element which is arranged in the cell culture dish. This results in the cell assemblages (e.g. EHTs) being produced no longer as described in DE 198 00 498 A1 as biconcave bodies attached by a hook and loop tape to two tubes but as continuous rings. The annular shape of the tissue results simply from the fact that a mixture of support substance and cells is poured into the cell culture dish in which at least one element is arranged. The EHT then grows as a continuous tape or around the element. It is particularly favorable if the element is arranged centrally and/or removably in the cell culture dish. It may moreover be possible for the element for example either to be screwed by means of a thread into the base of the cell culture dish or, in a particularly preferred embodiment, simply plugged into the base of the dish.

For it to be possible for a three-dimensional, circular muscle body or muscle ring to form in the cell culture dish, the element ought in every case to rise above the fill level of the mixture of support substance and cells (and in some circumstances a nutrient solution). If the length or height of the element is additionally also even higher than the rim of the cell culture dish, it is ensured in every case, irrespective of the fill level of the dish, that a three-dimensional, circular muscle body can form in the device of the invention. The element which can be inserted into the cell culture dish or is integrally connected to the latter thus preferably has a length or height $E_H$ which is greater than the fill level $F_H$ of the mixture, present in the cell culture dish, of support substance, cells and, where appropriate, nutrient liquid. It is preferred in particular that the height $E_H$ of the element is also greater than the height $R_H$ of the rim of the cell culture dish.

When the mixture of support substance and cells is poured into the cell culture dish, the mixture spreads out in the latter. The mixture is unable to spread at the point where the at least one element is arranged. The artificial cell tissue forms around the element. The finished artificial cell tissue can then be removed from the cell culture dish. If the element can be removed, the artificial cell tissue can be removed together with the element from the dish. This has a number of advantages compared with the previous manipulation (as described in DE 195 00 498 A1).

(1) The overall work involved becomes less because the following steps are omitted:

The assembly of the tubes with a metal bracket, the fastening of the tubes with hook and loop tape, the alignment of the device in the prefabricated wells in the cell culture dish and the troublesome pipetting of the mixture of support substance and cells into these wells. This also makes the production of larger test series less complicated and thus also more cost effective.

(2) The device of the invention can be used for an unlimited time, whereas the tubes fastened with hook and loop tape are subject to wear and can be employed a maximum of five times and then must be discarded and replaced by new ones.

(3) The uniformity of the annular constructs can easily be perfected because the device of the invention can be fabricated by machine and with minimal tolerances, whereas the components of the device described in DE 195 00 498 A1 must be fabricated manually and are thus subject to a not inconsiderable variability. The reproducibility of test series on use of the device disclosed in said published specification suffers from this.

(4) The annular constructs obtainable by use of the device of the invention are more stable and also more similar biologically to a natural heart than earlier cell tissues, because the nonphysiological junction of cell tissue with hook and loop tape or tubes is omitted.

(5) The manipulation of the annular constructs for investigations is simpler and easier than with the cell tissues obtainable previously (with hook and loop tape/tubes).

(6) The annular constructs can be miniaturized more easily than the cell tissues obtainable previously (with hook and loop tape/tubes).

The element arranged in the cell culture dish can also be designed to be in one piece (integral) with the cell culture dish. For it to be possible more easily to remove the constructs from the dish, however, it is preferred for the element and the culture dish to be separable from one another.

The at least one element which is arranged in the cell culture dish is advantageously designed to be cylindrical, resulting, when the shape of the cell culture dish is suitable, in an annular construct (three-dimensional, circular muscle body) with a round opening in the middle. The diameter of the cylindrical element is preferably between 3 and 8 mm, in particular about 5 mm. Further particularly suitable shapes for the element are frustoconical or oval. A particularly suitable material for constructing the element has proved in the case of a cell culture dish designed in one piece to be a permanently flexible material such as latex or silicone. If the element can be removed from the dish, the former is advantageously constructed from a nonadhesive, autoclavable, solid, inelastic material such as Teflon or Delrin. Teflon is polytetrafluoroethylene (PTFE) and is a registered trademark of DuPont. Delrin is likewise a registered trademark and can be purchased from DuPont. Delrin is a polyacetal plastic (polyoxymethylene) obtained by polymerization of anhydrous formaldehyde and having very good mechanical, thermal and chemical resistance.

Round or elliptical (oval) cell culture dishes are particularly suitable according to the invention because it is possible therewith most easily to produce round (circular) cell tissue assemblages. In the case of a round cell culture dish, the diameter thereof is advantageously between 10 and 20 mm, in particular 15 mm. In the case of an elliptical (oval) cell culture dish it is advantageous for the major axis to be between 10 and 30 mm, in particular 25 mm, and for the minor axis to be between 5 and 20 mm, in particular 15 mm, with the major axis always being larger than the minor axis.

The device of the invention is outstandingly suitable for the production of artificial, three-dimensional muscle tissue, especially cardiac tissue (EHT). Preferably employed for this purpose are collagen as support substance and muscle cells, specifically myocardial cells, as cells. It is possible in particular on use of the specific solutions described hereinafter also to culture mammalian muscle cell assemblages, in particular mammalian myocardial cell assemblages, in the device of the invention. Examples of suitable mammals are rats and mice. It is moreover a possible to employ as starting material either muscle cells, in particular myocardial cells, directly or stem cells which can be differentiated in vitro into muscle cells, in particular myocardial cells. Examples of the latter alternative are the cells which are obtained from pluripotent, mouse embryonic stem cells by means of a hanging drop method (method as described in the exemplary embodiment in the German patent DD 299 439 A5) and the cells which are obtained from mouse adult stem cells, each of which can be differentiated to muscle cells or myocardial cells.

A further important advantage of the device of the invention is the possibility of being able to arrange a plurality of devices directly in juxtaposition and/or succession. In principle any number of devices arranged in juxtaposition is moreover conceivable. However, it has proved to be advantageous to combine 24 devices (4×6) or a multiple thereof in a so-called multiwell plate. It is possible with these multiwell plates to produce many artificial cell tissues (especially EHTs) simultaneously, i.e. pour them and allow them to mature simultaneously. The mature cell assemblages can then be subjected without additional manipulations to further investigations; for example online force measurements can be carried out in the case of EHTs. Devices suitable for this purpose are described in more detail hereinafter.

The development of a multiwell plate for the production and measurement of EHTs represents a crucial step for the use of the EHTs in screening methods with high throughput ("high throughput screening") of medicaments in the widest sense. Besides the influence of classical chemical compounds, it is also possible to investigate the effects of a gene transfer, for example with recombinant adenoviruses, and of antisense oligonucleotides on myocardial cell function.

The present invention further relates to a solution for the cultivation of mammalian cardiomyocytes in a support substance and a method for the cultivation of a cell culture in a support substance using this solution. As already mentioned at the outset, it was not previously possible to provide a medium in which mammalian cardiomyocytes form a three-dimensional tissue. Earlier experiments were therefore carried out with chick myocardial cells. The solution of the invention for cultivating mammalian cardiomyocytes comprises a proportion of extracellular matrix of the Engelbreth-Holm-Swarm tumor (called "MATRIGEL®" for short). This MATRIGEL® can be obtained, for example, from Harbor Bio-Products, Tebu, Frankfurt (FRG). The solution preferably comprises at least as much MATRIGEL® for the latter to be present in the reconstitution mixture (i.e. the complete mixture of support substance solution (such as, for example, collagen solution), cell suspension (such as, for example, rat myocardial cell suspension) and nutrient solution) in a concentration of at least 5% by volume, in particular between 5 and 15% by volume. Very good results are obtained when MATRIGEL® is present in the reconstitution mixture in a concentration of about 10% by volume. This can be achieved for example in the following way. A two-fold concentrated nutrient medium (2×Dulbecco's modified essential minimal medium (2×DMEM), 20% horse serum, 4% chick embryo extract, 200 µg/ml streptomycin and 200 U/ml penicillin G) is mixed with a support substance solution (e.g. collagen solution) in the ratio of 50:50 parts by volume, so that the final concentration of nutrient medium in the mixture of support substance solution and nutrient medium is 1×DMEM, 10% horse serum, 2% chick embryo extract, 100 µg/ml streptomycin and 100 U/ml penicillin G. The mixture is then neutralized with a little alkali (e.g. 0.1 N NaOH). About 15% by volume MATRIGEL® solution are added to about 85% by volume of the neutralized mixture. Finally, the mixture containing support substance solution, nutrient medium and MATRIGEL® is mixed in the ratio of about 70:30% by volume with a cell suspension. The final mixture (reconstitution mixture) then contains about 10% by volume of MATRIGEL®.

It is self-evident that corresponding mixtures may also comprise other MATRIGEL® concentrations as long as it is ensured that the concentration in the reconstitution mixture is sufficiently high to bring about the growth of three-dimensional artificial tissues which comprise mammalian myocardial cells.

It was possible for the first time with the MATRIGEL® containing solution described above to form a three-dimensional artificial cardiac tissue with myocardial cells from neonatal rats in a support substance (collagen matrix).

The advantage of rat EHTs over chick EHTs is the fact that the former are derived from mammalian cells. This increases the comparability of the results obtained with humans. A further advantage is that the rat EHTs beat distinctly, specifically 2 to 3 times, more strongly than chick EHTs. Finally, the ratio of actively developed force to the passive basic tension is larger in rats than in chicks (1:2 to 1:1 in the rat, <1:10 in chicks).

The present invention further relates to a device for measuring isometric force parameters of cell cultures. This device comprises a cell culture tissue, at least one element which is arranged in the cell culture dish, a pressure recording unit and a unit for recording pressure changes. It is moreover possible for the cell cultures to be cultured directly in the cell culture dish, and transfer of the cultures from a culturing vessel into a measuring vessel is no longer necessary for the force measurements. The main operational step in the method disclosed in DE 195 00 498 A1, namely the removal of the relatively fragile cell culture (e.g. EHTs) from a dish and suspension in an organ bath, becomes redundant. In addition, an experimental variable is eliminated, namely the extent of the prestretching in the organ bath (prestretching in the sense of a percentage difference from the originally poured shape). It is also possible with the device of the invention to carry out continuous measurements of the force lasting days, whereas with the devices disclosed in the aforementioned German published specification measurements were possible for a few hours at best. In addition, the device of the invention allows force measurements in the nutrient medium, i.e. under the normal growth and maturation conditions, whereas an aqueous solution without amino acids, proteins, growth factors etc. is used in the conventional apparatus for measurements in an organ bath. Finally, the instrumental complexity is considerably less with the novel device of the invention than with the known device, allowing a considerable financial saving also to be achieved.

It may moreover be advantageous for the device of the invention for measuring isometric force parameters to have, besides the aforementioned components, an amplifying unit which amplifies the measured signal. Suitable pressure transducer units are, for example, strain gauges or tip catheters (e.g. Millar tip catheters).

It is preferred if, in a first embodiment of the device of the invention for measuring isometric force parameters, the cell culture dish and the element arranged therein are designed in one piece, i.e. if the element is an integral constituent of the cell culture dish. Since one of the main advantages of the device is that it no longer requires a transfer of the cell culture into a different vessel for measurements, it is also unnecessary for the element to be removable together with the cell culture from the culture dish.

As already described above for the device for producing a three-dimensional matrix or muscle body, the element arranged in the cell culture dish is preferably disposed in the middle (centrally). Concerning the shape of the element, it ought preferably to be cylindrical or frustoconical or have an oval (elliptical) cross section. In the case of a cylindrical design, the element preferably has a diameter in the range from 3 to 8 mm, in particular about 5 mm. A particularly suitable material for the element is a permanently flexible material such as, for example, latex or silicone.

In a second embodiment of the device of the invention for measuring isometric force parameters of cell cultures, it allows the prestretching of the EHTs before measurements of the force of contraction are carried out. In this case, the element should be removable from the cell culture dish and be constructed from a solid, inelastic material such as, for example, Teflon or Delrin. It is favorable for the material also to be nonadhesive and autoclavable, which applies to Teflon and Delrin.

The cell culture dish of the device of the invention for measuring isometric force parameters is preferably round with a diameter of from 10 to 20 mm, in particular about 15 mm. Oval (elliptical) cell culture dishes are also particularly suitable, and in this case the major axis of the ellipse is preferably between 10 and 30 mm, in particular 25 mm, and the minor axis is between 5 and 20 mm, in particular 15 mm, with the major axis always being larger than the minor axis.

To improve the structure of the cell culture to be cultured, it preferably comprises a support substance. If the cells in the cell culture are muscle cells, collagen is particularly suitable as support substance. It is possible to carry out in the device of the invention specifically on mammalian myocardial cells long-term investigations of the force developed under lifelike conditions.

In addition, the present invention also relates to a method for the measurable following of contractions of a cell tissue incorporated in a support substance. This entails first the provision of a cell culture dish which has an element arranged therein and into which a mixture of a support substance material and a cell tissue suspension is then introduced. The cell culture dish charged with support and cells is then incubated in an incubator until the contents of the cell culture dish have solidified. A nutrient solution is added to the cell culture dish before or else after this incubation step. The next step is to incubate the cell culture dish with the solidified mixture of support substance and cell tissue further for several days. It is then possible for the isometric force developed by the cell tissue to be determined by means of a pressure transducer unit and to be recorded by a data recording unit.

If the cells to be investigated are mammalian myocardial cells, the nutrient solution should comprise a sufficient amount of extracellular matrix of the Engelbreth-Holm-Swarm tumor (MATRIGEL®). Suitable nutrient solutions have already been described above. The complete mixture preferably comprises at least 5% by volume, in particular 5 to 15% by volume and specifically about 10% by volume of MATRIGEL®. It has also proved beneficial if 1×Dulbecco's modified essential minimal medium (1×DMEM), 10% horse serum, 2% chick embryo extract, 100 μg/ml streptomycin and 100 U/ml penicillin G are also present in the mixture.

Said method is suitable for example for force measurements on muscle cell tissue such as myocardial cells. It is possible with the method of the invention in combination with collagen as support substance and the solution described previously for the first time to carry out isometric force measurements on artificially produced, three-dimensional mammalian myocardial cell tissues.

The first incubation step in order to bring about solidification of the mixture of support substance and cell suspension usually lasts 1 to 2 hours. The temperature in the first incubation step is preferably about 37° C. The second incubation step lasts between 2 and 15 days, depending on the type of cell culture used, preferably 5 to 12 days, and in particular for mammalian myocardial cells 6 to 10 days.

Before the techniques described in DE 195 00 498 A1 were available, it was possible to measure the most important function of the heart, namely the force of contraction, reliably only on a complete isolated heart preparation (e.g. of a rat, guinea pig or frog) or on tissue strips from explanted animal hearts. The devices and methods in said published specification made it possible to dispense with animal experiments and, in particular, to be able to investigate better the significance of individual proteins in the myocardial cell for the regulation of the force of contraction. It was, however, not previously possible to cultivate mammalian myocardial cells, and the results obtained previously with chick myocardial cells are applicable only to a very limited extent to mammals and, in particular, to humans.

The invention now makes it possible for the first time to culture mammalian myocardial cells in tissue culture in such a way that a spontaneously and coherently beating association is produced. It is now possible with this model to manipulate very specifically the function of individual proteins in the mammalian heart in culture and to measure the force of contraction on cells manipulated in this way.

In addition, the invention also makes it possible for the first time to study accurately the interactive effect of the various cell types in the mammalian heart on the force of contraction. It is known that 80% of the cells in the heart are non-muscle cells, i.e., for example connective tissue cells, vascular cells or nerve cells. It is not as yet known what influence these cells have on the force developed in the mammalian heart. It is now possible in the system presented by the invention to mix diverse cell populations in various proportions and investigate what influence this has on the force of contraction.

It is additionally possible to investigate mechanisms of enlargement of mammalian hearts (hypertrophy) by the system resulting from the invention. In this connection it is possible to think of prestretching the cell culture tissue for different lengths of time and to different extents or incubating it with particular drugs. This causes an enlargement of the individual myocardial cells. It is now possible in the present system for the first time also to measure, simply and directly, the functional effect of enlargement of the mammalian heart under the experimental conditions.

The invention thus makes it possible for the first time to measure the isometric force of contraction on embryonic mammalian myocardial cells or, stated more generally, on cultivated mammalian muscle tissue separated from the organism. The invention thus makes it possible specifically to investigate effects of particular manipulations on mammalian muscle cells or of a mammalian myocardial enlargement on the force of contraction. Such questions are at the center of much of experimental research, i.e.

fundamental cardiovascular research and applied research with the aim of developing new drugs acting on the heart for the therapy of myocardial insufficiency and of cardiac arrhythmias.

It should be emphasized once again at this point that cardiovascular disorders are responsible for most of the deaths in the western world. Myocardial insufficiency is one of the commonest disorders of all, with an instance of about 3% in the German population. The treatment options have improved. Nevertheless, the 5-year mortality is still above 50% even now. This means that the development of medicaments able to improve myocardial insufficiency continues to represent a priority aim of health policy. The benefits of the present invention are to be seen in this connection in particular.

A further aspect of the invention is that the invention for the first time allows artificial rat cardiac tissue to be produced as tissue substitute, for example after a myocardial infarction. There are promising initial data that the ring EHTs produced according to the invention may adhere to the heart and possibly assist a diseased heart's own contraction. This will provide in certain circumstances unprecedented prospects for the treatment of heart diseases.

The present invention thus also relates to an artificially produced, three-dimensional muscle tissue comprising a support substance and muscle cells. The artificially produced, three-dimensional muscle tissue can be obtained by producing a mixture of a support substance and a nutrient solution, neutralizing the mixture, adding MATRIGEL® and a muscle cell suspension to the neutralized mixture, and subsequently incubating the mixture under conditions under which a three-dimensional muscle tissue can be produced. It is possible in principle to employ any type of muscle cell, but it is particularly preferred to use myocardial cells. The origin of the muscle cells is not critical. It is particularly preferred, especially in relation to obtaining information in relation to human heart disease, to employ mammalian muscle cells, for example from rats or mice. It is possible in this connection to take inter alia differentiated muscle cells, for example myocardial cells, as starting material, or else the pluripotent, mouse embryonic stem cells which have already been described above and which are able to differentiate into spontaneously pulsating myocardial cells (see DD 299 439 A5). The preferred support material is once again collagen, especially when myocardial cells or cells able to differentiate into myocardial cells are employed. The other parameters (nature and concentration of the nutrient solution, of the support substance, of the neutralizing agent, of the MATRIGEL® and of the muscle cell suspension, duration and temperature of the incubation step etc.) preferably correspond to the statements made in the claims, the introduction to the description and the examples of the present application.

The invention is explained in more detail hereinafter by means of the figures and examples.

Figure 1:
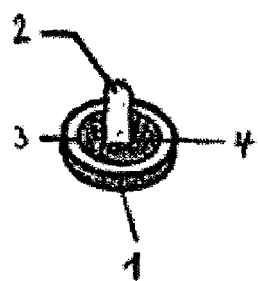
FIG. 1 shows a cell culture dish of the invention with an element arranged therein.

FIG. 1 shows a round cell culture dish 1 of the invention which comprises a centrally arranged cylindrical element 2. The cell culture dish 1 has a raised rim zone 3 and a recess zone 4 which can receive a mixture of support material, cell suspension and nutrient medium. The diameter of the cell culture dish 1 is 15 mm and the diameter of the centrally arranged cylindrical element is 5 mm. As is evident from FIG. 1, the central element 2 projects beyond the raised rim zone 3 of the cell culture dish 1. The height or length of the element $E_H$ is thus greater than the rim height $R_H$ of the cell culture dish 1, thus ensuring in every case that a three-dimensional, annular or circular muscle cell tissue can form in the cell culture dish.

Figure 2:
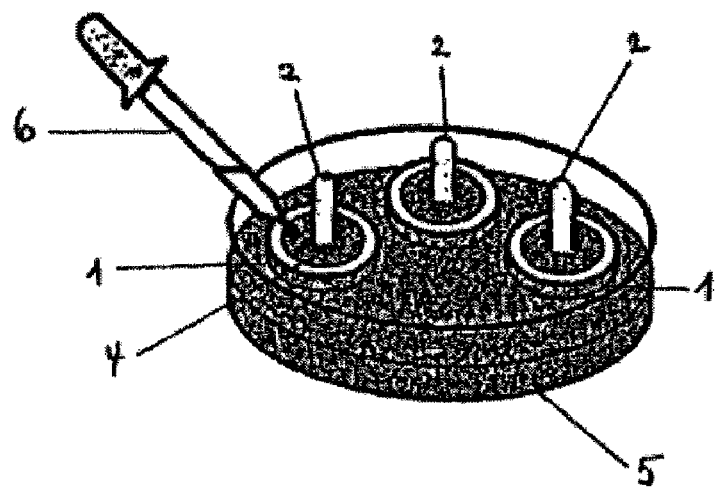
FIG. 2 shows a larger dish unit comprising a plurality of cell culture dishes of the invention as shown in FIG. 1.

Three of the cell culture dishes 1 shown in FIG. 1 are arranged in FIG. 2 in a larger dish unit 5. The dish unit 5 is a commercially available plastic Petri dish with a diameter of 10 cm. Up to 5 cell culture dishes 1 can be accommodated in such a dish unit 5. Also shown in FIG. 2 is a pipette 6 with which a cell suspension/collagen mixture is pipetted into a cell culture dish 1.

Figure 3:
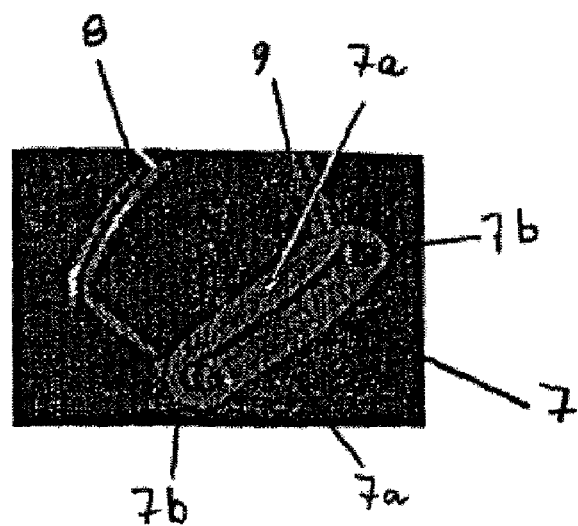
FIG. 3 shows an annular, artificial, three-dimensional cardiac tissue (EHT) obtained using the cell culture dish shown in FIG. 1.

FIG. 3 shows an artificial, three-dimensional, annular cardiac tissue (EHT) 7 as obtained after incubation for about 8 days in a cell culture dish 1 which has been charged with a mixture of collagen, a rat myocardial cell suspension, MATRIGEL® and nutrient medium. The EHT is tensioned between two retaining wires 8, 9 and has thus lost its original circular shape. The EHT shown in FIG. 3 has relatively long parallel sections 7a and narrow, curved sections 7b, with sections 7b extending around the retaining wires 8, 9.

Figure 4:
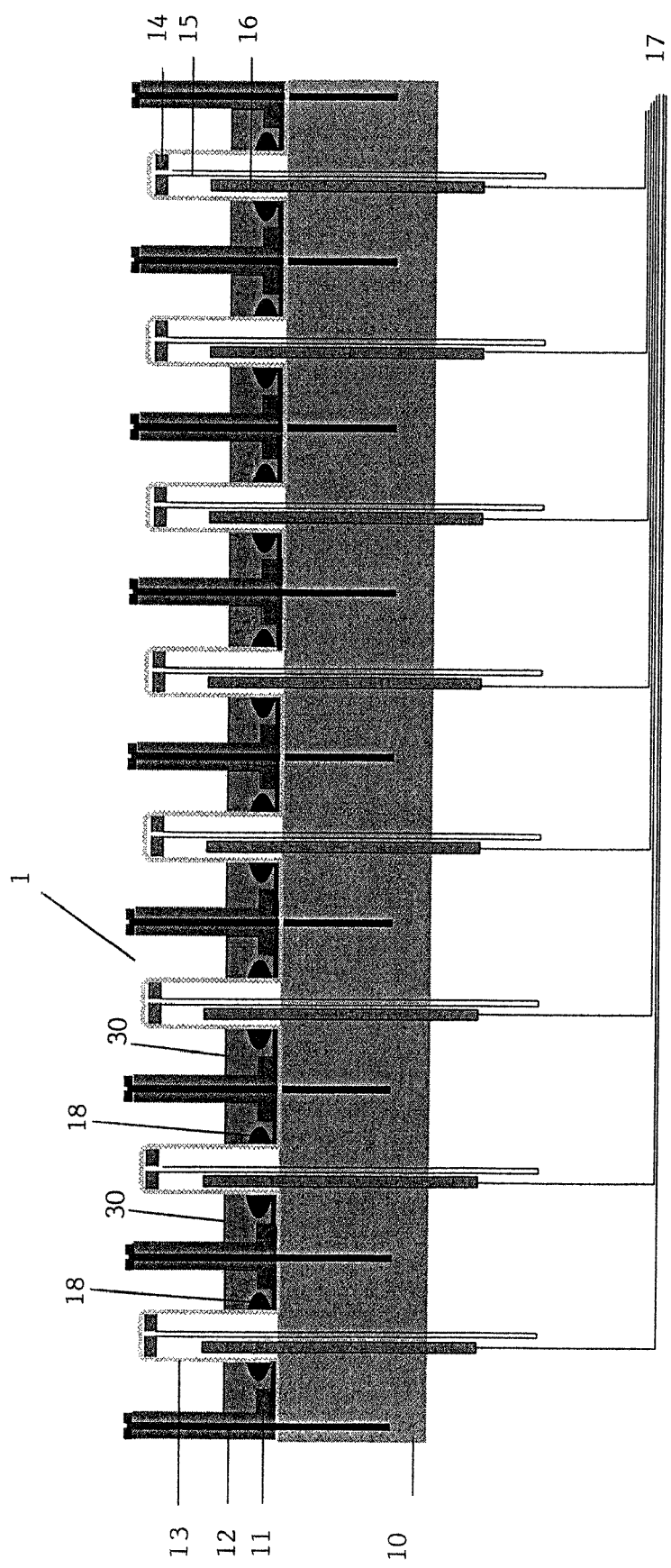
FIG. 4 shows a cross section through an embodiment of a multiwell plate of the invention having a device for measuring force.

FIG. 4 shows a cross section through a multiwell plate with which it is possible to carry out a pressure measurement on the annular EHTs shown in FIG. 3 (designated by the reference number 18 in FIG. 4). The individual EHTs are present in a nutrient medium 30. The reference number 10 designates a so-called Delrin support which acts as baseplate of the multiwell plate, and reference number 11 represents a Teflon mask. The Teflon mask 11 is screwed onto the Delrin support 10 with the stainless steel screw 12. A cylindrical, permanently flexible element 13 made of latex is arranged centrally in the cell culture dish 1. The element 13 has the shape of a hollow body. A support 14 is present in this hollow body and keeps the shape of the hollow body stable. In addition, a ventilation needle 15 and a Millar tip catheter 16 as pressure transducer unit are introduced from below through the Delrin support 10 into the hollow element 13. Leads 17 pass from the tip catheters 16 via an amplifier which is not shown to a recording unit (a personal computer) which is likewise not shown.

Figure 5:
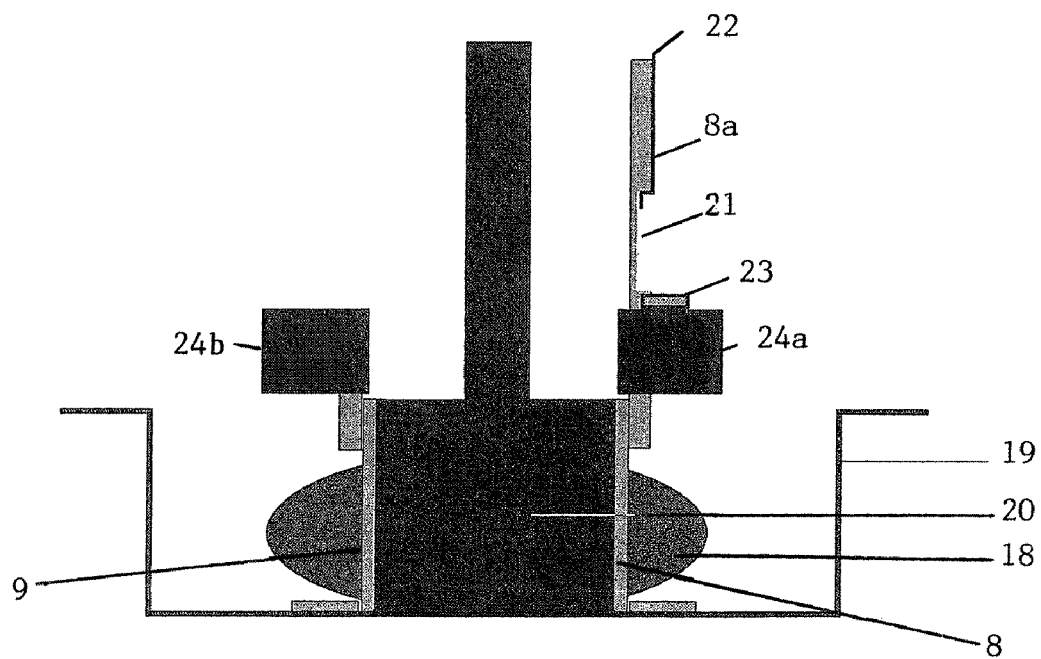
FIG. 5 shows a cross section through another embodiment of a cell culture dish of the invention with a device for measuring the force of contraction, shown at the instant of pouring the EHT.
Figure 6:
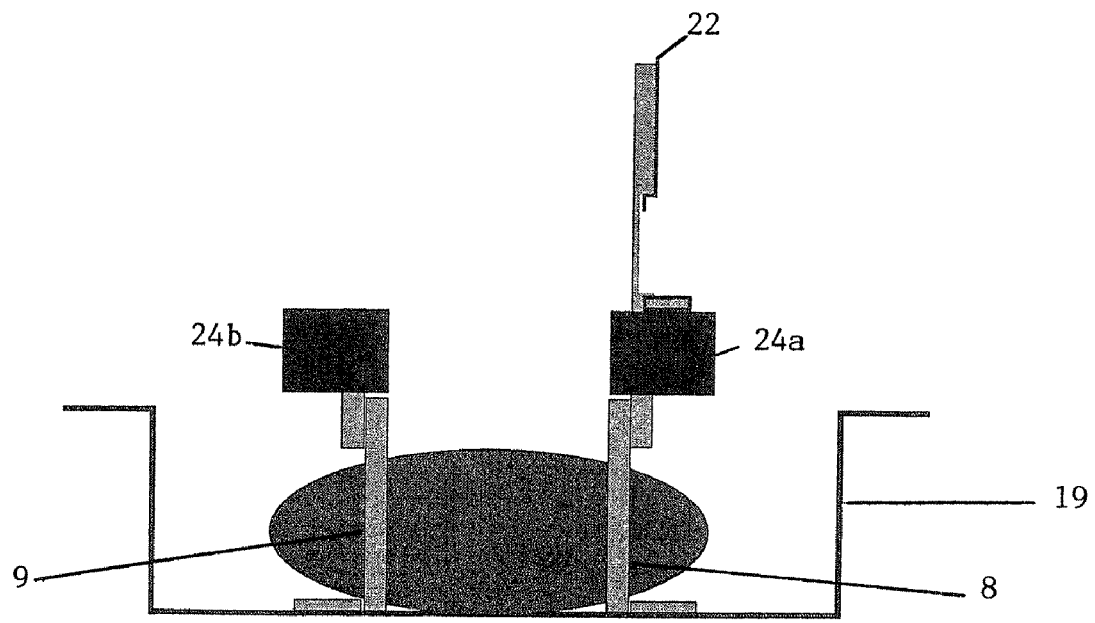
FIG. 6 shows the cell culture dish of the invention as shown in FIG. 5 after removal of the placeholder.

According to an alternative embodiment there is measurement on the EHTs produced according to the invention not of the pressure which develops but directly of the isometric force. For this purpose, an EHT ring 18 is poured around an element 20 in a cell culture dish 19 as shown in FIG. 5, which element has a cylindrical shape, is arranged centrally in the cell culture dish 19 and consists of a solid, inelastic material (Telfon). The cylindrical element 20 can be removed, after formation of the EHTs, from the cell culture dish 19 by being withdrawn upward. FIG. 6 shows the cell culture dish 19 without cylindrical element 20. The EHT is now held by two retaining wires 8 and 9 (see FIGS. 3, 5 and 6). The retaining wires 8 and 9 are arranged during the pouring and growth of the EHTs in two recesses in the cylindrical element 20, so that the outer contour of the cylindrical element 20 corresponds to a smooth cylinder wall despite the presence of the two retaining wires 8 and 9.

FIG. 5 further shows a unit with which the force of contraction developed by the EHTs can be measured. This unit has a strain gauge 21 which is arranged in the middle zone 8a of the retaining wire 8 and which is connected via a cable connection 22 and an amplifier, which is not shown, to a recording unit, which is likewise not shown. The retaining wire 8 has stable (rigid) lower and upper zones 8b, 8c which are connected together by a flexible part (middle zone 8a). The flexible middle part 8a of the retaining wire 8 consists of a permanently flexible material (in the present case of permanently flexible spring steel), and the stable (rigid) upper and lower sections 8b, 8c of the retaining wire 8 of stainless steel. The strain gauge 21 is bonded to the flexible middle part 8a of the retaining wire 8 and records the bending, caused by contraction of the cells, of the flexible part of the retaining wire.

Reference number 23 in FIG. 5 designates a fastener for the retaining wire on a stretching rod 24a. With this arrangement it is now possible to determine the force of contraction of EHTs directly where they are produced without needing to remove them, as formerly necessary (see DE 915 00 498 A1), from the culture dish and transferring them into an organ bath for the measurement.

A plurality of the cell culture dish 19 shown in FIG. 5 can be arranged in succession and/or juxtaposition, so that this embodiment of the invention can also be designed in the form of multiwell plates. In this case too, preference is again given to 24 (4×6) or a multiple thereof cell culture dishes arranged in juxtaposition and succession.

As already mentioned above, FIG. 5 represents the situation after the pouring of the EHT rings 18 around the cylindrical element 20 in the cell culture dish 19. The EHTs can then mature for some (about 3 to 4) days. After this, as is evident from FIG. 6, the cylindrical element 20 is removed, and the EHT rings are then retained inside by the retaining wires 8 and 9. The two retaining wires are then distanced from one another sufficient for the EHT ring 7, as shown in FIG. 3, to extend as an elongate oval which has two zones 7a arranged in parallel. In this position it is possible to measure the force developed by the EHT directly by bending the retaining wire 8 (in the described embodiment, the force is measured as indicated above via the retaining wire 8). For this purpose, the retaining wire 8 is bonded in its middle flexible zone 8a to a strain gauge 21 which is connected via an amplifier measuring bridge (not shown) to a recording instrument (personal computer, likewise not shown). The flexible zone 8a thus permits a force measurement to be carried out on individual EHTs.

Figure 7:
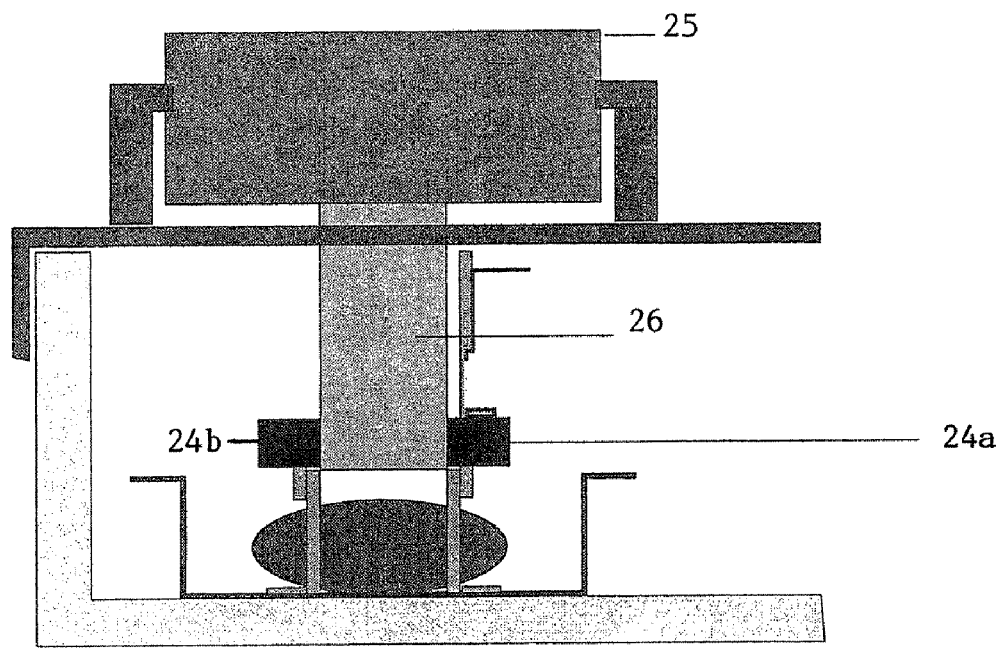
FIG. 7 shows the cell culture dish of the invention shown in FIG. 5 with a motorized unit for stretching the EHT.

To obtain optimal power yields it is necessary for the EHTs to be prestretched before measurement of the force of contraction thereof. A corresponding stretching motor is shown in FIG. 7. It has emerged in recent years that chronic stretching of EHTs leads to a considerable increase in the tissue development and increase in size of the individual myocardial cells and to an increase in the contractile force to three to five times that of EHTs which have not been prestretched. It is therefore more favorable for the force measurement not to be carried out directly after maturation of the EHTs. The beneficial effects of the prestretching appear after only about 24 hours. The prestretching is normally carried out for a period of about 1 to about 7 days because prestretching lasting longer than 7 days is associated with virtually no further increase in the force of contraction. The extent of the prestretching ought to be in the range from about 3 to about 20% of the initial length, with a prestretching of about 10% being particularly preferred.

Motorized prestretching is favorable. In the state of pouring and motorized stretching of the EHTs, the stretching rods 24a, 24b, to which the retaining wires 8 and 9 are affixed, are in a lower position. In the state of force measurement, the stretching rod 24a to which the retaining wire 8 with the flexible portion 8a is affixed, is in a raised state (FIG. 8) in which the upper stable (rigid) part 8c of the retaining wire is affixed to the stretching rod 24a and the flexible (middle) portion 8a is freely movable.

Figure 8:
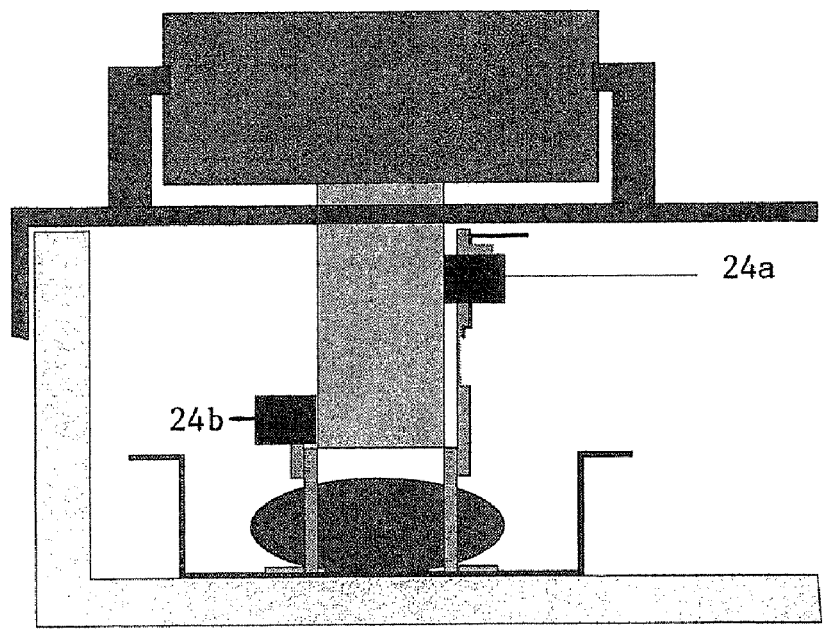
FIG. 8 shows the cell culture dish of the invention shown in FIG. 5 with a unit for measuring the force of contraction of the EHT.

In the state shown in FIG. 7 (with the stretching rod 24a in the lower position), the EHT can be stretched over a desired period (usually 1 to 7 days for rat EHT). In this phase, the stretching rod 24a remains in the low position so that it engages underneath the flexible portion 8a of the retaining wire 8, and thus no force acts on the flexible portion of the retaining wire. In FIG. 8, the stretching rod 24a has been raised above the flexible portion 8a of the retaining wire 8, so that the flexible portion of the retaining wire 8 is released and the force developed by the EHTs can be measured via the latter (bending of the flexible portion 8a with strain gauge 21). It is possible in principle to change backward and forward between stretching phase (stretching rod 24a underneath) and measuring phase (stretching rod 24 on top) as often as desired. Application of test substances, viruses, oligonucleotides etc. can take place in either phase.

In the case of a multiwell plate it is possible, as long as sufficient recording capacity is available, for the force measurement to take place simultaneously in all individual culture dishes (i.e. on all channels). If the storage capacity is less or if it is intended to reduce the technical complexity, it is also possible always to measure only some channels (e.g. 4 to 8) simultaneously, it being possible to switch between the individual channels of the complete multiwell plate by suitable software. This makes it possible, with certain gaps, for all the channels to be recorded continuously over any desired period.

Figure 9:
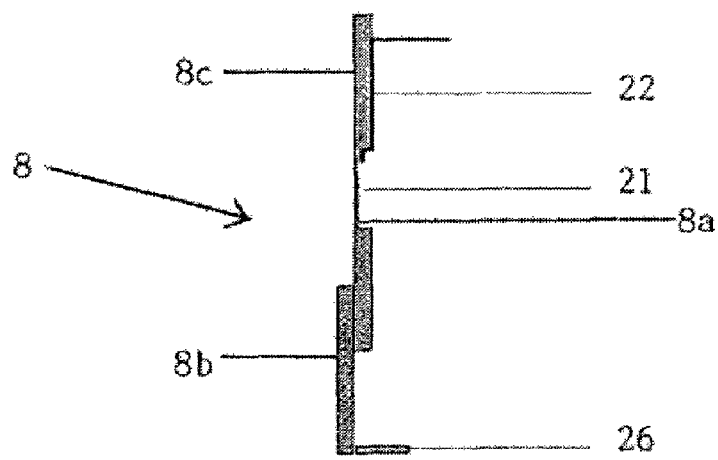
FIG. 9 shows a unit for measuring the force of contraction as used in FIG. 8.

FIG. 9 shows the retaining wire 8 once again in detail. The retaining wire 8 is stiff in the lower zone and provided with a securing means 26 to prevent slippage. The retaining wire 8 is flexible in the zone of the retaining wire in which the strain gauge 21 is arranged. A stiff section through which the cable connection 22 to the amplifier and recording unit runs follows above this flexible section again.

EXAMPLE 1

Cardiomyocytes were obtained from the hearts of newborn rats (total 2560 individual animals) 0 to 3 days old, specifically by a modification of the method described by Webster K A, Discher D J, Bishopric N H, 1993, Induction and nuclear accumulation of fos and jun proto-oncogens in hypoxic cardiac myocytes, J Biol Chem 268:16852-16858. The cells were preplated in 10% fetal calf serum for 1 to 2 h, and nonadherant cells were pelleted and suspended in culture medium (Dulbecco's modified essential minimal medium (DMEM), 10% horse serum, 2% chick embryo extract, 100 µg/ml streptomycin and 100 U/ml penicillin G). The cell density for pouring the EHTs was $10 \times 10^6$ cells/ml. The principal technique has already been described in Eschenhagen T, Fink C, Remmers U, Scholz H, Wattchow J, Weil J, Zimmermann H, Dohmen H H, Schafer H, Bishopric N, Wakatsuki T, Elson E L, 1997, Three-dimensional reconstitution of embryonic cardiomyocytes in a collagen matrix: A new heart muscle system. FASEB J 11:683-694.

In order to be able to define suitable conditions for culturing rat EHTs, the following parameters were investigated:

(1) Cell isolation method (trypsin, various collagenase types, dispase)

(2) Cell density ($0.8$-$1.3 \times 10^6$/EHT)

(3) Collagen concentration (0.8-1.3 mg/ml)

(4) Replacement of the cell/collagen reconstitution mixture by extracellular matrix from the Engelbreth-Holm-Swarm tumor (Harbor Bio-Products Tebu, Frankfurt (FRG); referred to as MATRIGEL® hereinafter) and serum complements from chick embryos and/or mammal.

A cell/collagen mixture stock solution was prepared by the standard method for 8 EHTs and stored on ice until poured. 1.33 ml of collagen type I (from rat tails; 3.6 mg/ml in 0.1% acetic acid; Upstate Biotechnology, Lake Placid N.Y.) were mixed with 1.33 ml of 2× concentrated culture medium (2×DMEM, 20% horse serum, 4% chick embryo extract, 200 µg/ml streptomycin, 200 U/ml penicillin G) and neutralized with 182 µl of 0.1 M NaOH. 0.48 ml of MATRIGEL® was added to this mixture, and 1.48 ml of the cell suspension, which corresponds to a total of $15 \times 10^6$ cells, were added to the mixture.

1 ml of the cell/collagen mixture was shaken in a cell culture dish (Delrin) with a diameter of 15 mm. The cylindrical element arranged centrally in the dish had a diameter of 5 mm and could be fastened by means of a screw to the base of the cell culture dish. The mixture was then incubated at 37° C. for 60 min until it was a gelatinous solid. 20 ml of culture medium were then added. The medium was replaced after a further incubation overnight and then every day.

Figure 10:
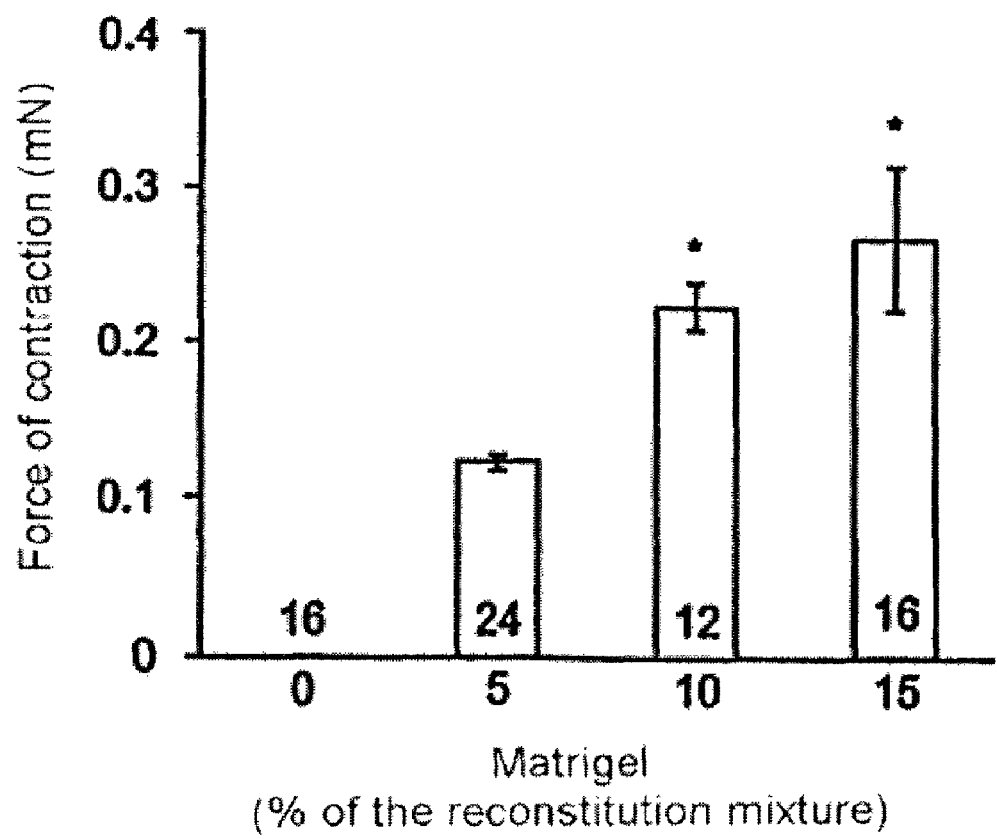
FIG. 10 shows a diagram revealing the dependence of rat EHT formation on the MATRIGEL® concentration in the reconstitution mixture.

Further investigations have revealed that it was the addition of MATRIGEL® which brought about the formation of spontaneously and coherently beating rat EHTs, and this effect was intensified further by the addition of chick embryo extract. In this connection, FIG. 10 shows the influence of increasing concentrations of MATRIGEL® in the reconstitution mixture. Rat EHTs were produced in the absence (0%) and in the presence of increasing concentrations of MATRIGEL® (5%, 10%, 15% of the reconstitution mixture). After cultivation for nine days, the contraction amplitude (force of contraction) was determined by means of an isometric force transmitting unit after adjustment to $L_{max}$ (length of maximum force developed). Rat EHTs without MATRIGEL® did not beat coherently and thus did not develop a measurable contraction amplitude. In order to obtain coherently beating EHTs it was thus necessary to add MATRIGEL® to the reconstitution mixture. The contraction amplitude increased with increasing MATRIGEL® concentrations, as is evident from the diagram shown in FIG. 10. In the diagram, the force of contraction is indicated in mN on the ordinate and the percentage proportion of MATRIGEL® in the reconstitution mixture is indicated on the abscissa. The asterisk on top of the columns designates a standard deviation P<0.05 toward 5%. The numbers indicated in the columns or above the abscissa correspond to the independent EHTs investigated.

EXAMPLE 2

This example is intended to describe the influence of stretching for a period lasting six days on the force of contraction developed by EHTs.

EHTs were cultivated as described above for four days and then subjected to an automated stretching carried out by a motor for six days. The extent of the stretching was between 1 and 20% of the original length of the EHTs, and another, unstretched group of EHTs was kept under otherwise identical conditions to serve as control group. The frequency of rotation of the stretching unit was 1.5 Hz. The complete device was kept in a $CO_2$ incubator at 37° C. The culture medium was changed every day.

Figure 11:
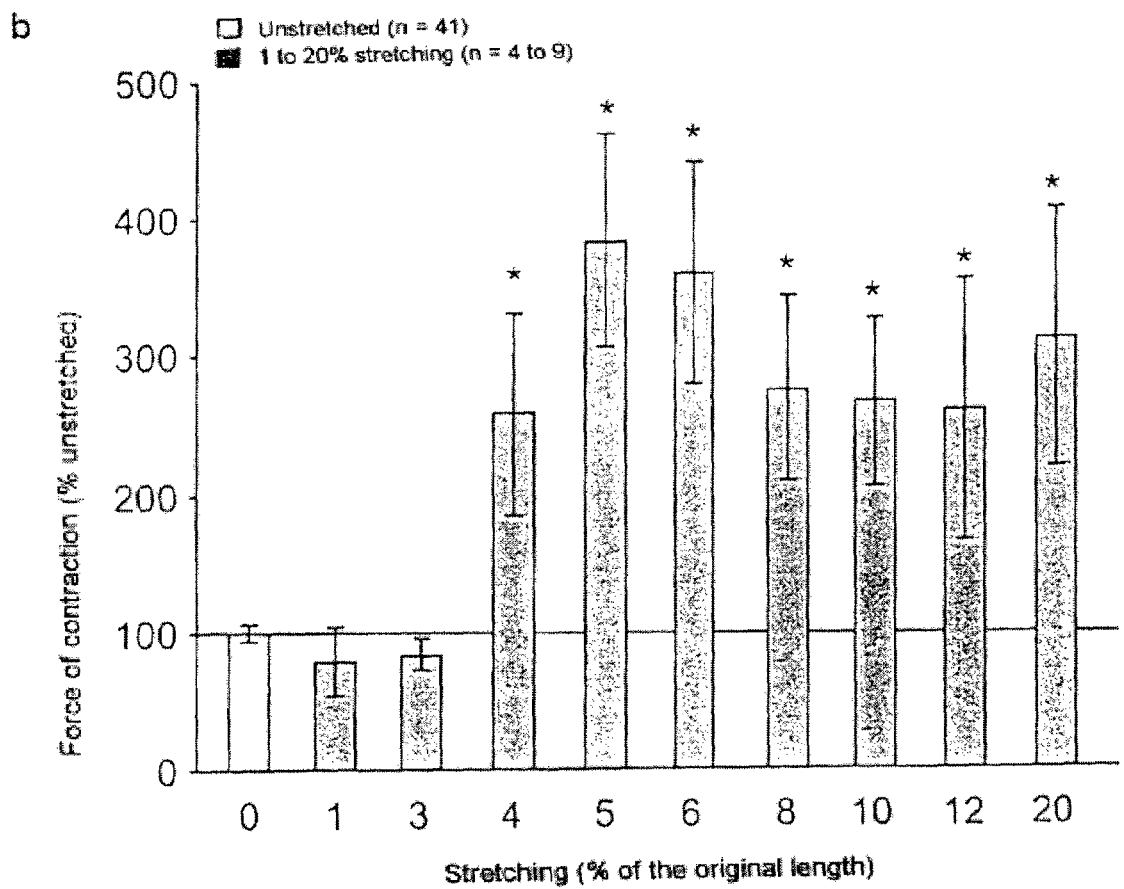
FIG. 11 shows a diagram showing the dependence of the force of contraction of EHTs on the prestretching of the EHTs.

As is evident from FIG. 11, a significant increase in the force of contraction can be seen only above 3% stretching and reaches a maximum at 5% stretching.

EXAMPLE 3

Figure 12A:
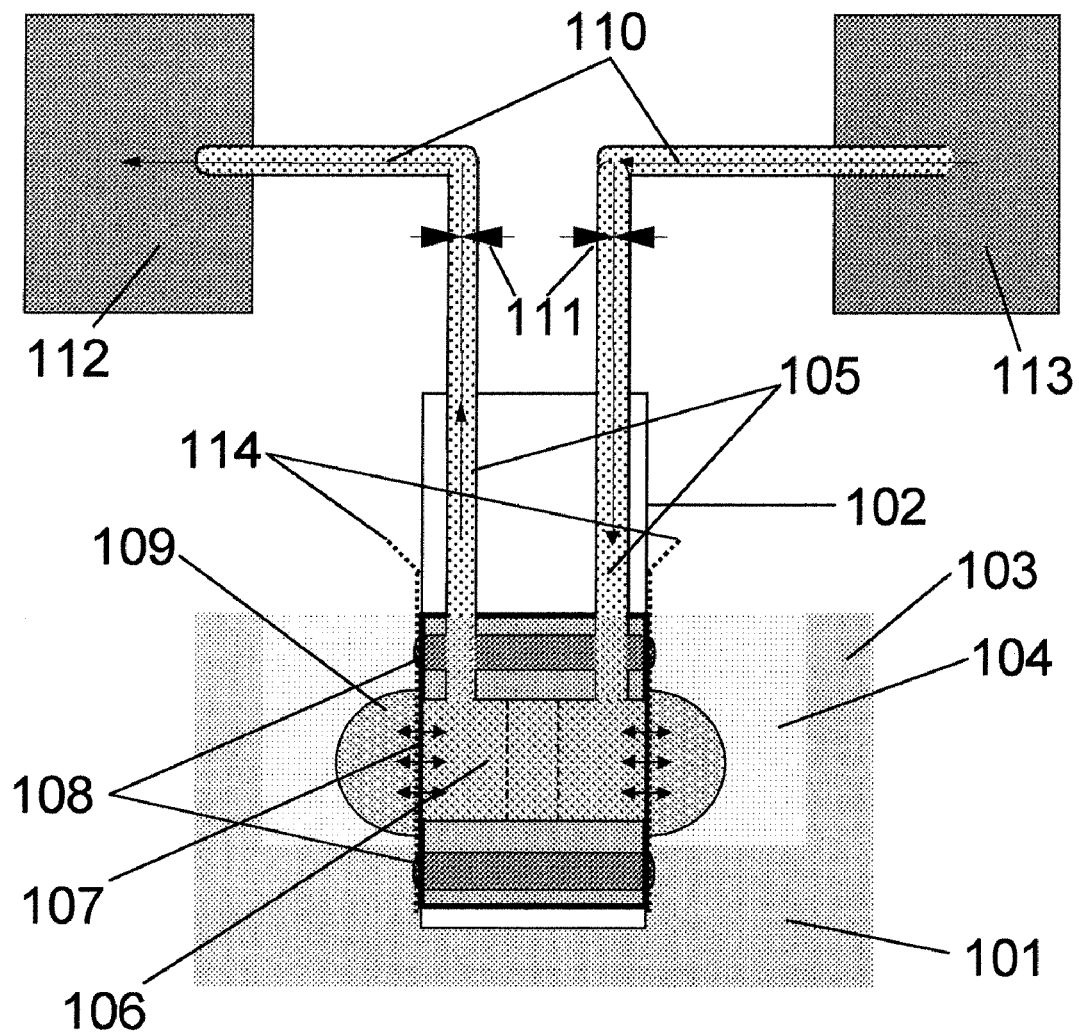
FIG. 12A shows a cross section through an embodiment of a combined device for producing a three-dimensional circular muscle body with a device for measuring isometric force parameters of the muscle body.

FIG. 12A shows a round cell culture dish 101 of the invention which comprises a centrally arranged, cylindrical element 102. The cell culture dish 101, made of Teflon, has a raised rim zone 103 and a recess zone 104 which can receive a mixture of support material, cell suspension and nutrient medium. Other suitable materials for the culture dish are, for example, silicone or other plastics. The diameter of the cell culture dish is 15 mm and the diameter of the centrally arranged, cylindrical element is 5 mm.

The cylindrical element 102 consists of a solid plastic and contains bores 105 and a cavity 106 which is open to the outside and is filled with a liquid. In the lower section of the cylindrical element 102, a tubular membrane 107, which is impermeable to the liquid but is elastic, is pulled around the element 102 and seals the open cavity 106 to the outside. The elastic membrane is made of silicone. Another suitable material for the elastic membrane is, for example, latex. The elasticity of the membrane 107 is indicated in FIG. 12A by the arrows in the lower zone of the cylindrical element 102. The membrane is firmly connected via fastenings 108 to the cylindrical element 102. The liquid has a low viscosity and density.

The reference number 109 designates an artificial, annular cardiac tissue (EHT) which has formed around the cylindrical element 102 in the cell culture dish 101 after incubation for about 8 days, the cell culture dish having been charged with a mixture of collagen, a rat myocardium suspension, MATRIGEL® and nutrient medium.

The bores 105 and the cavity 106 closed by the membrane 107 form together with the tubes or inelastic tubing 110 fitted to the bores a hydraulic system. The arrows in the inelastic tubing 110 indicate the direction of flow of the liquid. The system additionally includes the shut-off valves 111, a device for pressure measurement 112 and a device for pressure generation 113.

Figure 12B:
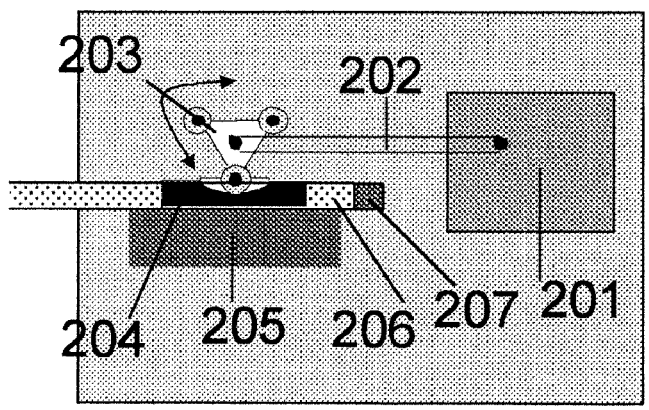
FIG. 12B shows a cross section through a device for generating pressure.

The device for pressure generation 113 may be, for example, a hydraulic pump as depicted in FIG. 12B. The pressure generation device 113 has a motor 201, a unit for force transmission 202, a rotating roller system 203, a flexible tubing 204, an abutment 205 and an inelastic tubing 206 whose end is provided with a closure 207. It is also possible to use a tube in place of the inelastic tubing. The curved arrow in FIG. 12B indicates the direction of rotation of the roller system 203.

The system (model) functions in the following way. If the shut-off valve 111 of the outflow (shown on the left in FIG. 12A) arm of the tubing system 110 is closed while the valve in the right arm is open, a pressure can be generated in the hydraulic system by the device for pressure generation 113 and leads to an expansion of the membrane 107 forming a liquid-tight closure of the cavity 107. The muscle ring 109 can thus be overstretched by rhythmic pressure generation.

If the shut-off valve 111 of the inflow (shown on the right in FIG. 12A) arm is closed and the valve in the outflow (right) arm is opened, it is possible for the force of the contracting muscle ring (EHT) 109 to be measured quantitatively in the device for pressure measurement 112 via the reduction in volume of the cavity 106.

This system (model) thus has the advantage that the production and the overstretching of the muscle ring, and the force measurement can take place in one and the same device without the need to transfer the muscle rings from a pouring chamber into an overstretching or measuring chamber.

In contrast to an arrangement in which a muscle ring is tensioned as oval between two hooks and in which therefore the cells located at the ends of the muscle ring are stretched or contract perpendicular to the direction of overstretching/measurement, it is possible with a completely circular arrangement of the muscle ring for each cell to be stretched and contribute to the reduction in volume of the ring. The resulting muscle ring is therefore more homogeneous and thus tends to reflect the natural muscle. The force measurement is more accurate because, compared with the conventional apparatus, firstly it is possible to measure contraction of more (and in the ideal case of all) cells in the ring, and secondly the contraction of cells which contract perpendicular to the direction of measurement and thus lead to unwanted oscillations can be avoided.

The arrangement of the invention can be miniaturized, and a plurality of the arrangements can be combined for example in 24- or 48-well cell culture dishes. It is possible by connection in parallel or connection in series of such arrangements for measured signals to be averaged and/or amplified.

In a particular embodiment, the membrane 107 can be a piezo film which, on contraction, induces a voltage which is proportional to the force and which in turn can be measured by means of electrodes. A force measurement of this type has advantages in relation to sensitivity and inertia compared with hydraulic measurement.

A further possibility is completely to replace the hydraulic system by arranging, in place of the cavity 106, a body which changes its volume as a function of an applied voltage, which can be applied and measured via electrodes. The overstretching of the muscle ring is effected by rhythmic application of a voltage which leads to an expansion of the body in the direction of the muscle ring. The force measurement in turn takes place by measurement of the voltage induced by the reduction in volume. A system of this type can further be miniaturized and is simpler to produce and better to reuse than systems employed to date.

It is additionally possible to attach electrode 114 which can be used to cause the muscle cells to contract electrically. In the case of myocardial cells, for example, the electrical stimulation can be employed in place of the mechanical overstretching for maturation of the muscle ring. Since skeletal muscle cells and smooth muscle cells do not, in contrast to myocardial cells, contract spontaneously, the electrical stimulation can be employed for maturation of the muscle rings and for inducing contraction. The force measurement can then take place as described above.

The invention claimed is:

1. An artificially produced, three-dimensional muscle tissue comprising a support substance and muscle cells, the tissue produced by:
producing a first mixture of a support substance solution and a nutrient solution;
neutralizing the first mixture;
adding extracellular matrix from the Engelbreth-Holm-Swarm tumor and a suspension of muscle cells to the first mixture to produce a second mixture, wherein the second mixture comprises at least 5% by volume of the extracellular matrix from the Engelbreth-Holm-Swarm tumor;

subsequently incubating the second mixture under conditions such that an artificial, three-dimensional muscle tissue is produced; and prestretching the muscle tissue to an additional 4-20% of its initial length.

2. The artificially produced, three-dimensional muscle tissue as claimed in claim 1, wherein said muscle cells are mammalian muscle cells.

3. The artificially produced, three-dimensional muscle tissue as claimed in either of claims 1 or 2, characterized in that the muscle tissue is myocardial tissue.

4. A method for augmenting the function of diseased muscle tissue, the method comprising:

adding to the diseased muscle tissue an artificially produced, three-dimensional muscle tissue comprising a support substance and muscle cells, the tissue produced by:

producing a first mixture of a support substance solution and a nutrient solution;

neutralizing the first mixture;

adding extracellular matrix from the Engelbreth-Holm-Swarm tumor and a suspension of muscle cells to the first mixture to produce a second mixture, wherein the second mixture comprises at least 5% by volume of the extracellular matrix from the Engelbreth-Holm-Swarm tumor;

subsequently incubating the second mixture under conditions such that an artificial, three-dimensional muscle tissue is produced; and prestretching the muscle tissue to an additional 4-20% of its initial length.

5. The method of claim 4, wherein said muscle cells are mammalian muscle cells.

6. The method of claim 4 or 5, characterized in that the muscle tissue is myocardial tissue.

7. A method for replacing diseased muscle tissue, the method comprising:

replacing the diseased muscle tissue with an artificially produced, three-dimensional muscle tissue comprising a support substance and muscle cells, the tissue produced by:

producing a first mixture of a support substance solution and a nutrient solution;

neutralizing the first mixture;

adding extracellular matrix from the Engelbreth-Holm-Swarm tumor and a suspension of muscle cells to the first mixture to produce a second mixture, wherein the second mixture comprises at least 5% by volume of the extracellular matrix from the Engelbreth-Holm-Swarm tumor;

subsequently incubating the second mixture under conditions such that an artificial, three-dimensional muscle tissue is produced; and prestretching the muscle tissue to an additional 4-20% of its initial length.

8. The method of claim 7, wherein said muscle cells are mammalian muscle cells.

9. The method of claim 7 or 8, characterized in that the muscle tissue is myocardial tissue.

10. An artificially produced, three-dimensional muscle tissue comprising a support substance and muscle cells, the tissue produced by:

producing a first mixture of a support substance solution and a nutrient solution;

neutralizing the first mixture;

adding extracellular matrix from the Engelbreth-Holm-Swarm tumor and a suspension of muscle cells to the first mixture to produce a second mixture, wherein the second mixture comprises at least 5% by volume of the extracellular matrix from the Engelbreth-Holm-Swarm tumor;

subsequently incubating the second mixture in a circular form under conditions such that an artificial, three-dimensional muscle tissue is produced; and prestretching the muscle tissue to an additional 4-20% of its initial length.

11. The artificially produced, three-dimensional muscle tissue as claimed in claim 10, wherein said muscle cells are mammalian muscle cells.

12. The artificially produced, three-dimensional muscle tissue as claimed in either of claims 10 or 11, characterized in that the muscle tissue is myocardial tissue.

13. A method for augmenting the function of diseased muscle tissue, the method comprising adding to the diseased muscle tissue the artificially produced, three-dimensional muscle tissue as claimed in claim 10.

14. A method for replacing diseased muscle tissue, the method comprising replacing the diseased muscle tissue the artificially produced, three-dimensional muscle tissue as claimed in claim 10.

15. A method for producing a three-dimensional artificial muscle tissue, the method comprising:

producing a first mixture of a support substance solution and a nutrient solution;

neutralizing the first mixture;

adding extracellular matrix of the Engelbreth-Holm-Swarm tumor and a suspension of muscle cells to the first mixture to produce a second mixture, wherein the second mixture comprises at least 5% by volume of the extracellular matrix of the Engelbreth-Holm-Swarm tumor;

incubating the second mixture in a circular form under conditions such that an artificial, three dimensional muscle tissue is produced; and prestretching the muscle tissue to an additional 4-20% of its initial length.

* * * * *

UNITED STATES PATENT AND TRADEMARK OFFICE
CERTIFICATE OF CORRECTION

| | | |
|---|---|---|
| PATENT NO. | : 7,618,452 B2 | Page 1 of 1 |
| APPLICATION NO. | : 10/182131 | |
| DATED | : November 17, 2009 | |
| INVENTOR(S) | : Thomas Eschenhagen | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1530 days.

Signed and Sealed this

Fourteenth Day of December, 2010

David J. Kappos
*Director of the United States Patent and Trademark Office*